United States Patent [19]
Shimada et al.

[11] Patent Number: 6,093,534
[45] Date of Patent: Jul. 25, 2000

[54] MONOCLONAL ANTIBODY SPECIFICALLY RECOGNIZING ADENO-ASSOCIATED VIRUS CAP PROTEIN

[75] Inventors: Takashi Shimada, Tokyo; Hidekazu Kuma; Yosuke Suzuki, both of Ibaraki-ken, all of Japan

[73] Assignee: Hisamitsu Pharmaceutical Co., Inc., Saga, Japan

[21] Appl. No.: 08/913,667

[22] PCT Filed: Mar. 15, 1996

[86] PCT No.: PCT/JP96/00655

§ 371 Date: Sep. 11, 1997

§ 102(e) Date: Sep. 11, 1997

[87] PCT Pub. No.: WO96/29349

PCT Pub. Date: Sep. 26, 1996

[30] Foreign Application Priority Data

Mar. 17, 1995 [JP] Japan .................................... 7-059149

[51] Int. Cl.[7] .............................. C12Q 1/70; C12N 5/20; C07K 16/08
[52] U.S. Cl. .............................. 435/5; 435/332; 435/339; 530/388.1; 530/388.3; 530/413
[58] Field of Search ................................ 435/5, 332, 339; 530/388.1, 388.3, 413

[56] References Cited

U.S. PATENT DOCUMENTS 5,436,146 7/1995 Shenk et al. ........................ 435/172.3

OTHER PUBLICATIONS

Hardy, R.R., "Complement Fixation by Monoclonal Antibody-Antigen Complexes", Handbook of Experimental Immunology (4th Ed. by D.M. Weir), 1(40):40.1–40.12 (1986).

Hardy, R.R., "Purification and Characterization of Monoclonal Antibodies", Handbook of Experimental Immunology (4th Ed. by D.M. Weir), 1(13):13.1–13.13 (1986).

Kipps, T.J. and Herzenberg, L.A., "Schemata for the Production of Monoclonal Antibody–Producing Hybridomas", Handbook of Experimental Immunology (4th Ed. by D.M. Weir), 4(108):108.1–108.9 (1986).

Oi, V.T. and Herzenberg, L.A., "Immunoglobulin–Producing Hybrid Cell Lines", Selected Methods in Cellular Immunology (Ed. Barbara B. Mishell and Stanley M. Shiigi), 17:351–372 (1980).

Kabat, E.A. and Mayer, M.M., "Antibodies and Their Characterization", Experimental Immunochemistry (2nd Ed. by Kabat and Mayer), 7: 326–360 (1961).

Kohler et al., Nature, v. 256, p. 495 (1975).

Milstein et al., Nature, v. 266, p. 550 (1977).

Trempe, J.P. et al. "Alternate mRNA splicing is required for synthesis of adeno–associated virus vP1 capsid protein," J. Virol., v. 62, No. 9, pp. 3356–3363, (1988).

Cassinotti, P. et al. "Organization of hte adeno–associated virus)AAV) capsid gene: mapping of a monor spliced mRNA coding for virus capsid protein 1, " Virology, v. 167, No. 1, p. 176–184 (1988).

Hunter, L.A. et al. "Colocalization of adeno–associated virus rep and capsid proteins in the nuclei of infected cells," J. Virol., v. 66, No. 1, p. 317–324.

Wistuba, A. et al. "Intermediates of adeno–associated virus type 2 assembly: identification of soluble complexes containing rep and cap proteins," J. Virol., vol. 69, No. 9, p. 5311–5319, (1995).

Kohler et al., Eur. J. Immounol., vo. 6, p. 511 (1977).

Walsh, Nature, v. 226, p. 495 (1977).

Hunter et al., "Colocalization of adeno–associated virus Rep and capsid proteins in the nuclei in infected cells", Journal of Virology, vol. 66, No. 1, pp. 317–324, Jan. 1992.

Mendelson et al., "Replication of adeno–associated virus type 2 in human lymphocytic cells and interaction with HIV–1", Virology, 187, 453–463, 1992.

Trempe et al., "Alternate mRNA splicing is required for synthesis of adeno–associated virus VP1 capsid protein", Journal of Virology, vol. 62, No. 9, 3356–3363, Sep. 1988.

Liddell et al., "Production of Monoclonal Antibodies", pp. 25–44 in Antibody Technology, BIOS Scientific Publishers, Oxford, 1995.

Primary Examiner—Donna C. Wortman
Assistant Examiner—Brenda G. Brumback
Attorney, Agent, or Firm—Morrison & Foerster, LLP

[57] ABSTRACT

A monoclonal antibody specifically recognizing adeno-associated virus CAP protein, which is produced by hybridomas obtained by fusing lymphocytes prepared from a mammal which has been immunized with the adeno-associated virus CAP protein or a recombinant thereof as an antigen with a myeloma cell line. The monoclonal antibody of the present invention is a novel antibody and capable of specifically recognizing the adeno-associated virus CAP protein. Thus, it is applicable to the detection of the adeno-associated virus and the purification of adeno-associated virus vectors for gene therapy.

4 Claims, 2 Drawing Sheets

MONOCLONAL ANTIBODY SPECIFICALLY RECOGNIZING ADENO-ASSOCIATED VIRUS CAP PROTEIN

TECHNICAL FIELD

This invention relates to a novel monoclonal antibody. More particularly, it relates to a monoclonal antibody specifically recognizing the adeno-associated virus CAP protein, a hybridoma cell line producing this monoclonal antibody, and a method of detecting the adeno-associated virus and a method of purifying a virus vector for gene therapy by using the above-mentioned monoclonal antibody.

BACKGROUND ART

There have been made a number of attempts to transfer genes for gene therapy. At the present time, it is the most accustomed method therefore to use virus vectors, since a high gene transfer efficiency can be achieved thereby. For example, retrovirus vectors and adenovirus vectors are now under development. However, it is reported that use of these vectors is accompanied by various problems such that the gene thus transferred can be expressed only at a low efficiency or hardly integrated into chromosome, or there arises a cytotoxicity, etc.

The adeno-associated virus (AAV) vector may be cited as an example of the virus vectors attracting public attention in recent years. AAV is also called an adeno-satellite virus and falls into the category of the genus Parvovirus B, i.e., the smallest particles among animal viruses. It is known that this virus is a defective virus lacking the ability to self-proliferate and depends on the adenovirus in proliferation. Different from double-stranded DNA viruses, namely, the adeno-associated virus is a single-stranded DNA virus characterized by encoding exclusively a capsid protein. Since the transcription and replication of this virus per se depend on a cell system, it can proliferate exclusively in cells infected with adenovirus.

It is also reported that AAV tends to be integrated into a specific region in the long arm of the human 19th chromosome, which makes this virus further noteworthy.

As described above, the adeno-associated virus cannot replicate except in cells infected with adenovirus. To use an AAV vector as a virus vector for gene therapy, it is therefore needed to purify the AAV vector. That is to say, a general method for constructing an AAV vector comprises co-transfecting appropriate cells such as HeLa cells with a packaging plasmid prepared by deleting ITR (inverted terminal repeat) from the wild type AAV gene and a vector plasmid containing a gene having IDR introduced thereinto, simultaneously infecting these cells with adenovirus and then repeating freeze-thawing to thereby give the virus vector thus produced. Since not only the AAV recombinant but also the adenovirus are produced in this process, it is required to establish a method for purifying the AAV recombinant alone. Although it is suggested to carry out the purification with the use of a monoclonal antibody specific to AAV, no monoclonal antibody specific to AAV has been obtained so far.

DISCLOSURE OF THE INVENTION

Accordingly, an object of the present invention is to develop a monoclonal antibody which specifically recognizes the adeno-associated virus CAP protein. Another object of the present invention is to provide a hybridoma cell line capable of producing the above-mentioned monoclonal antibody, and a method of detecting the adeno-associated virus and a method of purifying a virus vector by using the above-mentioned monoclonal antibody.

Accordingly, the present invention provides a monoclonal antibody specifically recognizing the adeno-associated virus CAP protein, which is produced by hybridomas obtained by fusing lymphocytes prepared from a mammal which has been immunized with the adeno-associated virus CAP protein or a recombinant thereof as an antigen with a myeloma cell line.

The present invention further provides a hybridoma cell line capable of producing the above-mentioned monoclonal antibody specifically recognizing the adeno-associated virus CAP protein.

The present invention furthermore provides a method of detecting the adeno-associated virus and a method of purifying a recombinant adeno-associated virus vector for gene therapy by using the above-mentioned monoclonal antibody specifically recognizing the adeno-associated virus CAP protein.

BEST MODE FOR CARRYING OUT THE INVENTION

Figure 1A:
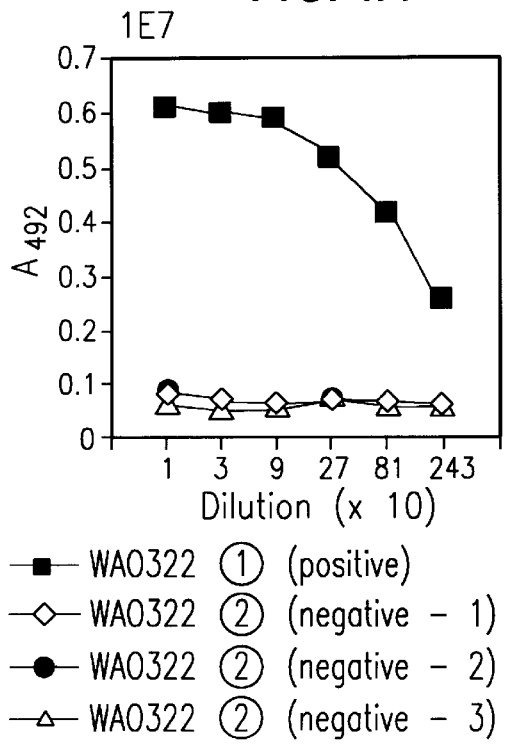
FIGS. 1A–1D are graphs showing the reactivity of each of the monoclonal antibodies (1E7, 1E9, 1G5 and 1G12) to the antigen.

Now, the present invention will be described in detail. A process of producing the monoclonal antibody of the present invention is typified by the following one.

First, an immune animal is immunized with an adeno-associated virus CAP protein recombinant employed as the antigen. After boosting with the antigen, antibody-producing cells are taken out from the immune animal. Next, these antibody-producing cells are fused with myeloma cells to thereby construct hybridomas. Then these hybridomas are subjected to screening so as to separate hybridomas capable of producing the desired monoclonal antibody therefrom. The hybridomas thus selected are then incubated to thereby give the desired monoclonal antibody.

As the antigen to be used in the production of the monoclonal antibody of the present invention, use can be made of the adeno-associated virus CAP protein or a recombinant thereof. Namely, it is possible to use therefore the CAP protein obtained by infecting host cells with the virus, collecting the viral particles thus proliferating and purifying the same. Alternatively, use can be made therefore of an adeno-associated virus CAP protein recombinant obtained by gene recombination techniques which are well known by those skilled in the art (e.g., those including steps of isolation and cloning of a DNA encoding the CAP protein, construction of an expression plasmid with the use of this DNA and an appropriate expression vector, transformation of the plasmid into a host and incubation of the transformant under appropriate conditions).

In the above-mentioned process of the production of the monoclonal antibody, the animal to be immunized with the antigen may be an arbitrary one selected from among those commonly employed as an immune animal, for example, mammals such as mouse, rat, rabbit, goat, sheep, bovine and equinum. Among these animals, it is preferable to use mouse or rat as the immune animal from the viewpoints of the availability of the myeloma cells to be fused with the antibody-producing cells (lymphocytes) obtained by the immunization, etc.

The line of the mouse or rat is not particularly restricted. In the case of mouse, for example, use can be made of A, AKR, BALB/c, BDP, CBA, CE, C3H, C57BL, C57BR, C57L, DBA, FL, HTH, HT1, LP, NZB, NZW, RF, RIII, SJL, SWR, WB, 129, etc. In the case of rat, on the other hand, use can be made of Low, Lewis, Spraque, Daweley, ACI, BN, Fischer, etc. Among these lines, BALB/c mouse and Low rat are particularly preferable as the immune animal when the fusion compatibility with the myeloma cells as will be described hereinafter is taken into consideration. At the step of immunization, it is preferable that the mice or rats are from 5 to 12 weeks in age, still preferably from 6 to 8 weeks. When the animals are younger than 5 weeks, it is difficult to immunize them. When the age of the animals exceeds 12 weeks, on the other hand, there arises a tendency that the immunization efficiency is decreased.

The immune animals can be immunized with an adeno-associated virus CAP protein recombinant employed as the antigen by an arbitrary immunization technique known per se without any problem. For example, the immunization technique may be selected from those described in detail in Weir D. M., "Handbook of Experimental Immunology", Vols. I, II and III, Blackwell Scientific Publications, Oxford (1987); Kabat. E. A. and Mayer, M. M., "Experimental Immunochemistry", Charles C. Thomas Publisher Spigfield, Illinois (1964); etc. Among these immunization techniques, those appropriately employed in the present invention will be described in detail hereinafter.

(1) Construction of Hybridoma Cell Lines Producing Monoclonal Antibodies Specific to the Adeno-associated Virus CAP Protein The antigen may be administered either intracutaneously or intraperitoneally. To elevate the immunization efficiency, however, it is preferable to combine these administration routes together. When the antigen is intracutaneously administered in the former half followed by the intraperitoneal administration in the latter half or it is intraperitoneally administered at the final administration alone, namely, the immunization efficiency can be particularly elevated.

The immunizing schedule cannot be determined in a wholesale manner but varies depending on the type of the immune animal, individual, etc. In general, it is preferable that the antigen is administered 3 to 6 times at intervals of 2 to 6 weeks, still preferably 3 or 4 times at intervals of 2 to 4 weeks. An excessively high administration frequency causes a waste of the antigen, while excessively long administration intervals are associated with an aging of the immune animal and, in its turn, a poor activation of cells. Therefore, these cases are both undesirable.

The immunizing dose of the antigen to the immune animal cannot be determined in a wholesale manner but varies depending on the type of the immune animal, individual, etc. In general, it ranges from 5 to 500 μg, preferably from 10 to 100 μg. With respect to the boosting schedule, the boosting is effected from 1 to 6 weeks, preferably from 2 to 4 weeks and still preferably from 2 to 3 weeks after the final immunization of the immune animal with the antigen. It is preferable that spleen cells involving the antibody-producing cells are taken out from the immune animal 1 to 10 days, still preferably 2 to 5 days and still preferably 2 or 3 days thereafter. It is not preferable to perform the boosting longer than 6 weeks or shorter than 1 week after the immunization, since the boosting cannot achieve any satisfactory effect in such a case. Also, it is not preferable to take out the spleen cells within 1 day after the boosting, since the effect of the boosting is worsened in such a case.

The dose of the antigen in the boosting cannot be determined in a wholesale manner but varies depending on the type of the immune animal, individual, etc. In general, it ranges from 5 to 500 μg, preferably from 10 to 100 μg and still preferably from 10 to 50 μg in the case of mouse. It is not preferable to administer the antigen in an unnecessarily large dose, since the immunizing effects are worsened and, moreover, undesirable effects are exerted on the immune animal thereby.

The antibody-producing cells may be separated from the spleen cells, which have been aseptically taken out from the above-mentioned immune animal, by an arbitrary method known per se without restriction [see, Kohler et al., Nature, 256, 495 (1975); Kohler et al., Eur. J. Immunol., 6, 511 (1977); Milstein et al., Nature, 266, 550 (1977); and Walsh, Nature, 226, 495 (1977)]. For example, use can be made of a general separation method which comprises cutting the above-mentioned spleen cells into pieces, filtering these pieces through a stainless mesh and then suspending them in Eagle's minimum essential medium (MEM).

Next, the antibody-producing cells thus obtained are subjected to cell fusion with myeloma cells to thereby give hybridomas for acquiring the monoclonal antibody.

The myeloma cells to be fused with the antibody-producing cells to thereby give hybridomas are not particularly restricted but selected from the myeloma cell lines which have been conventionally employed in cell fusion and are known per se. For example, mouse or human myeloma cells are usable therefor. Particular examples of these cell lines include those originating in mouse such as X63-Ag8 (abbreviated as X63; the same will apply hereinafter), NSI-Ag4/1 (NS1), P3X63-Ag8. U1 (P3U1), X63-Ag8.654 (X63·654), SP2/0-Ag14 (SP2/0), MPC11-45.6TG1.7 (45.6TG), F0, S149/5XX0, BU.1, etc.; those originating in rat such as 210. RSY3. Ag1.2.3 (Y3), etc.; those originating in human being such as U-226AR (SKO-007), GM1500·GTG-A12 (GM1500), UC729-6, LICR-LOW-HMy2 (HMy2), 8226AR/NIP4-1 (NIP41), etc. It is preferable that the myeloma cell line to be used herein is an HGPRT [hypoxanthine guanine phosphoribosyl transferase] deficient strain for which the method of screening hybridomas after the cell fusion has been established. The cell lines cited above are all HGPRT-deficient ones.

In the process of producing the monoclonal antibody of the present invention, the above-mentioned antibody-producing cells can be fused with the myeloma cells by a method known per se. For example, use can be made therefor of a chemical method wherein the antibody-producing cells are mixed with the myeloma cells in a solution of a polymer (polyethylene glycol, etc.) at a high concentration or a physical method with the use of electrical stimulation (electroporation). The process can be appropriately performed under such conditions that the survival rate of the cells is not so remarkably lowered [see, for example, Wier, D. M., "Handbook of Experimental Immunology", Vols. I, II and III, Blackwell Scientific Publications, Oxford (1987); Kabat. E. A. and Mayer, M. M., "Experimental Immunochemistry", Charles C. Thomas Publisher Spigfield, Ill. (1964)].

The above-mentioned chemical method will be now described in greater detail. When polyethylene glycol is employed as a solution of a polymer at a high concentration, namely, it has been a practice to incubate the antibody-producing cells together with the myeloma cells in polyethylene glycol with a molecular weight of 1,500 to 6,000, preferably 2,000 to 4,000, at a temperature of 30 to 40° C., preferably 35 to 36° C. for 1 to 10 minutes, preferably for 5 to 8 minutes.

Although the hybridomas obtained by the above-mentioned cell fusion may be selected by an arbitrary method without restriction, the HAT (hypoxanthine aminopterin thymidine) selection method is usually employed therefor. The HAT selection method is described in detail in, for example, Kohler et al., Nature 256, 495 (1975) and Milstein et al., Nature, 266, 550 (1977).

This method is effective in obtaining hybridomas by using myeloma cells of an HGPRT-deficient strain which cannot survive in the presence of aminopterin. Namely, the hybridomas obtained by the above-mentioned cell-fusion are continuously incubated in the HAT medium (a medium containing hypoxanthine, aminopterin and thymidine). Thus, hybridomas tolerant to aminopterin can selectively survive and proliferate in the medium.

The above-mentioned hybridomas can be cloned by an arbitrary known method such as the methylcellulose method, the soft agarose method or the limiting dilution analysis without restriction [see, for example, Barbara, B. M. and Stanely, M. S. "Selected Methods in Cellular Immunology", W. H. Freeman and Company, San Francisco (1980)]. Among these method, it is particularly preferable to use therefor the limiting dilution analysis. In this method, first a microplate is inoculated with feeder cells such as fibroblasts originating in fetal rat, normal mouse spleen cells, thymocytes or ascites fluid cells. Separately, the hybridomas are preliminarily diluted with a medium to give a concentration of 0.2 to 0.5 cell/0.2 ml. This diluted hybridoma suspension is then pipetted into the microplate at a rate of 0.1 ml/well. About ⅓ of the medium is replaced by a fresh one at definite intervals, for example, every 3 days. After continuing the incubation for about 2 weeks, clones of the hybridomas are proliferated.

The hybridomas thus selected may be incubated to thereby efficiently produce the monoclonal antibody. It is preferable that the hybridomas capable of producing the desired monoclonal antibody are screened prior to the incubation. The screening can be performed by a method known per se. For example, use can be made therefor of the solid phase EIA (enzyme immunoassay) method, the liquid phase EIA method, the solid phase RIA (radio immunoassay) method, the liquid phase RIA method, the fluorescent antibody method, etc. It is preferable in the present invention to use the solid phase EIA method. In the solid phase EIA method, the adeno-associated virus CAP protein is immobilized in each well of a microplate and then the hybridoma culture supernatant containing the antibody is added thereto. After thus performing the antigen-antibody reaction, the well is washed and a labeled antibody such as a peroxidase-labeled mouse IgG antibody is added thereto. After washing the well again, hydrogen peroxide employed as the substrate and a color developing agent are added thereto. Then the absorbance is measured to thereby determine the activity. Thus, the hybridomas capable of producing the desired monoclonal antibody can be screened. This screening may be carried out either before or after cloning the hybridomas as described above.

(2) Production of Monoclonal Antibody to the Adeno-associated Virus CAP Protein and Method of Purifying the Same In the process of producing the monoclonal antibody of the present invention, the incubation of the hybridomas is not particularly restricted but can be carried out in a conventional manner. For example, the hybridomas may be incubated in the same medium as the one employed in the cloning as described above. Alternatively, the monoclonal antibody can be obtained in a large amount by intraperitoneally injecting the hybridomas into a mouse and collecting the monoclonal antibody from the ascites fluid of the animal. In the case of the intraperitoneal administration, a larger volume of the ascites fluid can be obtained by administering a mineral oil such as 2,6,10,14-tetramethylpentadecane (pristane) to the animal 3 to 7 days before the intraperitoneal administration. In this method, an immunosuppressant is intraperitoneally injected into a mouse of the same line as that of the hybridomas preliminarily. After thus inactivating T cells, $10^6$ to $10^7$ clone cells are suspended in a serum-free medium (0.5 ml) and intraperitoneally injected into the animal. Then the abdomen swells up within 10 to 20 days in usual and the ascites fluid thus pooled is collected from the mouse. By using this method, the monoclonal antibody can be obtained at an about 100 times or more higher concentration than the one in the culture medium.

The monoclonal antibody thus obtained may be purified by an arbitrary method without restriction. For example, it can be purified by the methods described in Weir, D. M., "Handbook of Experimental Immunology", Vols. I, II and III, Blackwell Scientific Publications, Oxford (1987). Typical examples of these methods include ammonium sulfate salting out, gel filtration, ion exchange chromatography and affinity chromatography.

Among these methods, the ammonium sulfate salting out is repeated 1 to 6 times, preferably 3 to 6 times. Thus the monoclonal antibody can be purified. However, there arises a problem that the monoclonal antibody can be purified by this method at only an extremely poor yield. Thus, the highly purified monoclonal antibody can be obtained at a high yield by carrying out the ammonium sulfate salting out 1 or 2 times and then subjecting the crude monoclonal antibody thus obtained to at least one treatment, preferably two treatments, selected from among gel filtration, ion exchange chromatography, affinity chromatography, etc.

The ammonium sulfate salting out may be combined with other methods in, for example, the following orders: (1) ammonium sulfate salting out/ion exchange chromatography/gel filtration; (2) ammonium sulfate salting out/ion exchange chromatography/affinity chromatography; (3) ammonium sulfate salting out/gel filtration/affinity chromatography; etc.

Among all, the combination (3) is the most desirable procedure in order to obtain the highly pure monoclonal antibody at a high yield.

The hybridomas producing the above-mentioned monoclonal antibody can be stored in a frozen state in liquid nitrogen or a freezer at −80° C. or below.

Particular examples of the hybridomas thus produced include hybridomas HAAV-1G12, HAAV-1E9, HAAV-2H7, HAAV-2H9, HAAV-1G5, HAAV-3E7 and HAAV-1E7 which have been deposited in accordance with Budapest Treaty at National Institute of Bioscience and Human-Technology, Agency of Industrial Science and Technology at 1–3, Higashi 1 chome Tsukuba-shi Ibaraki-ken, Japan, respectively under the accession numbers:

FERM BP-5460 (Domestic accession number: FERM P-14764, the same will apply hereinafter);

FERM BP-5461 (FERM P-14765);

FERM BP-5462 (FERM P-14766);

FERM BP-5463 (FERM P-14767);

FERM BP-5464 (FERM P-14768);
FERM BP-5465 (FERM P-14769); and
FERM BP-5466 (FERM P-14770); all of which were domestically deposited on Feb. 15, 1995 and were transferred to international depositions on Mar. 11, 1996.

The novel monoclonal antibodies produced by the process of the present invention as described above include those produced by the following hybridoma cell lines constructed by fusing the spleen lymphocytes of mouse immunized with the adeno-associated virus CAP protein recombinants with myeloma cells:

FERM BP-5460 (FERM P-14764);
FERM BP-5461 (FERM P-14765);
FERM BP-5462 (FERM P-14766);
FERM BP-5463 (FERM P-14767);
FERM BP-5464 (FERM P-14768);
FERM BP-5465 (FERM P-14769); and
FERM BP-5466 (FERM P-14770).

It is well known that a monoclonal antibody is usable in detecting the antigen specifically recognized thereby and purifying this antigen. For example, such an antigen can be detected and purified by using immunoassay techniques, affinity chromatography techniques, etc. which are well known by those skilled in the art.

Sandwich immunoassay may be cited as an example of the immunoassay techniques. In this method, two monoclonal antibodies to the adeno-associated virus CAP protein are employed. More particularly speaking, the first monoclonal antibody is bonded to the surface of a solid phase support. Next, a sample for detecting the antigen to the antibody is added thereto and the antigen-antibody reaction is performed. Thus, the antigen, if contained in the sample, is bonded to the first monoclonal antibody on the solid phase support. After an appropriate period of reaction time, the support is washed to thereby eliminate the sample. Then the second monoclonal antibody is added thereto and reacted therewith. This second monoclonal antibody recognizes an antigen determinant different from the one recognized by the first monoclonal antibody and binds thereto. After an appropriate period of reaction time, washing is performed to eliminate the second monoclonal antibody, and detection is then performed in association with the presence or absence of the second monoclonal antibody to thereby detect the presence or absence of the antigen in the sample. For example, an enzyme catalyzing a color development reaction can be preliminarily bonded to the second monoclonal antibody. In this case, the color development substrate is added after the reaction between the second monoclonal antibody and the antigen and washing as described above. Thus, the presence or absence of the antigen can be detected depending on the color development. Alternatively, the second antibody may be detected by taking advantage of affinity in, for example, an avidin-biotin system.

The affinity chromatography techniques are also well known by those skilled in the art. In a typical case, a monoclonal antibody specific to the adeno-associated virus CAP protein is covalently bonded to a solid phase support and thus immobilized followed by packing into a column. Then a sample containing the antigen to be purified is poured into the column. Thus the antigen is bonded to the antibody immobilized on the support, while other substances cannot be bonded to the immobilized antibody. After washing the column under appropriate conditions, therefore, the antigen to be purified alone remains in the column. Subsequently, an appropriate eluent is poured into the column so as to loosen the bond between the antigen and the antibody and thus the antigen is eluted to thereby give the purified antigen.

More particularly speaking, an appropriate host (HeLa cells, etc.) is transfected with a vector plasmid and a packaging plasmid and, at the same time, infected with an adenovirus followed by repeated freeze-thawing. The thus obtained sample containing an AAV recombinant and the adenovirus is then poured into the above-mentioned column. Thus the AAV recombinant can be purified.

To further illustrate the present invention in greater detail, the following Examples will be given. Needless to say, it is to be understood that the present invention is not restricted thereto.

Example 1
(Immunization, feeding and blood collection of mouse)

In this Example, use was made of the following antigens:
WAO322-1: a recombinant of the adeno-associated virus CAP protein (provided by Prof. Takashi Shimada, Nippon Medical University);
WAO322-2: (negative-1): adenovirus type-5 protein (provided by Prof. Takashi Shimada, Nippon Medical University);
WAO322-2: (negative-2): mouse serum protein; and
WAO322-2: (negative-3): fetal calf serum protein.
WAO322-1: is an antigen for immunizing and screening, while WAO322-2 (negative-1 to negative-3) are those for confirming the occurrence of the cross reaction.

Immunization, feeding and blood collection of mice were performed in the following manner.

250 $\mu$g of WAO322-1 was suspended in 0.5 ml of physiological saline. The obtained suspension was well mixed with the same volume of Freund's complete adjuvant (FCA; manufactured by DIFCO LABORATORIES) to thereby give a water-in-oil type emulsion. Then this emulsion was intracutaneously administered to five BALB/c female mice (aged 6 weeks, Japan Charles River) in a dose of 50 $\mu$g of the antigen per animal, i.e., priming.

2 weeks after the priming, 125 $\mu$g of WAO322-1 was suspended in 0.5 ml of physiological saline. The obtained suspension was well mixed with the same volume of Freund's incomplete adjuvant (FCA; manufactured by DIFCO LABORATORIES) to thereby give a water-in-oil type emulsion. Then this emulsion was intracutaneously administered to the above mice in a dose of 25 $\mu$g of the antigen per animal, i.e., the first boosting.

2 weeks after the first boosting as described above, the second boosting was performed by preparing an oil-in-water type emulsion followed by the intracutaneous administration similar to the case of the first boosting.

Further, the final immunization was carried out by suspending 50 $\mu$g of WAO322-1 in 0.5 ml of physiological saline and intraperitoneally administering the suspension to the animals. 3 days after the final immunization, the spleen was taken out from each animal and employed in cell fusion.

During the immunization period, the mice were kept in polycarbonate cages placed in a feeding room under regulated conditions, i.e., at a temperature of 24±2° C., under illumination for 12 hours per day (illumination time by a fluorescent light: from 7 a.m. to 7 p.m.) and ventilating 15 times per hour. These animals were maintained on a solid feed (CE-2, manufactured by Clea Japan) and drinking water (well water containing about 2 ppm of sodium hypochlorite) ad libitum. The cages were replaced twice a week and the feeding room was cleaned everyday. The animals were distinguished from each other by marking the tail with a felt-tip pen. A label showing the title of the test, sex and individual number of the animal and the immunizing schedule was put on the front of each cage.

7 days after each of the first and second boostings, the blood was orbitally collected and the antibody titer of the serum was determined by the ELISA method as will be described in Example 3 hereinafter. Table 1 summarizes the results. After being immunizing thrice, all of the 5 mice showed high antibody titers. Among these animals, the mouse No. 4 showed the highest absorbance at a dilution of 27,000-fold. Thus the spleen cells of this mouse were employed in the construction of hybridomas.

TABLE 1

| | Antibody titer of mouse antiserum | | |
|---|---|---|---|
| | Boosting (1) | Boosting (2) | |
| Immunization Individual no. of mice | Antibody titer (dilution) | Antibody titer (dilution) | $A_{492}$ at dilution of 27000 |
| 1 | 27000 | 81000 | 0.866 |
| 2 | 27000 | 81000 | 1.044 |
| 3 | 9000 | 27000 | 0.636 |
| 4 | 27000 | 81000 | 1.075 |
| 5 | 27000 | 27000 | 0.735 |

Example 2
(Cell fusion and cloning)

The blood of the mouse No. 4 in the above Example 1 was collected from the axillary vein under ether anesthesia and the serum was employed as a positive control in the screening. First, the spleen of the mouse was aseptically taken out. After washing with phosphate-buffered saline (PBS) and serum-free RPMI1640 medium (manufactured by Sanko Junyaku K.K.) containing kanamycin (400 μg/ml), the spleen was cut at several sites. Then the spleen cells were pushed out by using the frosted part of a slide glass and washed with a Tris-NH$_4$Cl solution to thereby eliminate erythrocytes therefrom. Thus the spleen cells for cell fusion were prepared.

The spleen cells obtained above were mixed with mouse myeloma cells P3x63Ag8U1 (P3U1) at a ratio of 5:1 (spleen cells: myeloma cells). After sufficiently eliminating the medium, these cells were fused with each other by incubating together in 1 ml of 50% polyethylene glycol 4000 (manufactured by Sigma Chemical) at 37° C. for 2 minutes.

Next, these cells were washed with serum-free RPMI1640 medium and then suspended in 10% FBS (fetal bovine serum, manufactured by Bio Whittaker) RPMI1640 medium supplemented with HAT ($1 \times 10^{-4}$ M of hypoxanthine, $4 \times 10^{-7}$ M of aminopterin and $1.6 \times 10^{-5}$ M of thymidine; manufactured by Shigma Chemical)(HAT medium).

These cells were pipetted into a 96-wells culture plate (665180, manufactured by Greiner Labortechnik) at a ratio of $3 \times 10^5$ cells/well and incubated at 37° C. in the presence of 7% of $CO_2$. 3 days after the cell fusion treatment, 0.1 ml of HAT medium was added to each well and the incubation was further continued.

7 days after the cell fusion, the antibody titer of the culture supernatant was measured by the ELISA method as will be described in Example 3 hereinafter, thus performing the first screening. Then the cells in wells reacting exclusively with WAO322$^{-1}$ were subjected to the limiting dilution analysis (1 cell/well), thus performing the first cloning.

Subsequently, the screening and cloning were repeated and thus 7 types of monoclonal hybridomas (1E7, 1E9, 1G5, 1G12, 2H7, 2H9 and 3E7) were obtained. In the cloning, use was made as a feeder layer of mouse peritoneal exudate cells ($10^4$ cells/well) which had been incubated at 37° C. in the presence of 7% of $CO_2$ overnight.

Example 3
(Measurement of antibody titer)

The measurement of the mouse serum antibody titers during the immunization period and the screening of the culture supernatant were carried out in accordance with the ELISA method which will be described hereinbelow. WA0322-1 or WA0322-2 was used as the solid phase antigen to the ELISA plate. Further, the culture supernatant of the myeloma P3U1 or a normal non-immune mouse serum was employed as a negative control, while the anti-WA0322 mouse serum collected in Example 2 was diluted 20,000- or 40,000-fold and employed as a positive control in the screening. Procedures of ELISA method:

(1) Adsorption of Antigen onto each Well of ELISA Plate (formation of solid phase antigen)

0.1 ml of a solution (5 μg/ml) of WA0322-1 or WA0322-2 diluted with PBS was added to each well of a 96-wells flat-bottomed ELISA plate (FALCON 3912, manufactured by Becton Dickinson Labware) and then allowed to stand at 4° C. overnight.

(2) Washing

Each well of the ELISA plate was washed with PBS containing 0.05% of Tween 20 (Tween-PBS) thrice.

(3) Inhibition of Nonspecific Adsorption (blocking)

To inhibit nonspecific adsorption, each well was filled up with 0.2 ml of Tween-PBS containing 0.5% of BSA and allowed to stand at 37° C. for 1 hour.

(4) Washing

Each well of the ELISA plate was washed with Tween-PBS thrice.

(5) Reaction Between Antiserum and Culture Supernatant

The antisera, which had been subjected to three fold serial dilution starting from 1,000-fold with the use of Tween-PBS containing 0.1% of BSA, the control serum and the culture supernatants were added each in an amount of 0.1 ml/well and then allowed to stand at room temperature for 2 hours to thereby perform the antigen-antibody reaction.

(6) Washing

Each well of the ELISA plate was washed with Tween-PBS thrice.

(7) Reaction With Enzyme (HRP)-labeled Antimouse IgG Rabbit IgG 0.1 ml of a solution (1 μg/ml) of enzyme-labeled antimouse IgG rabbit IgG diluted in Tween-PBS containing 0.1% of BSA was added to each well and allowed to stand at room temperature for 1 hour.

(8) Washing

Each well of the ELISA plate was washed with 0.05% Tween 20-PBS 5 times.

(9) Enzyme Reaction 0.1 ml of a color developing solution [10 mg of o-phenylenediamine, 10 ml of 50 mM disodium hydrogenphosphate/24 mM citrate buffer (pH 5.0), 120 μl of 1.7% solution of hydrogen peroxide] was added to each well and the enzyme reaction was effected at room temperature.

(10) Termination of Enzyme Reaction

The enzyme reaction was terminated by adding 0.05 ml of 6 N sulfuric acid to each well.

(11) Measurement of Absorbance

Immediately after the termination of the enzyme reaction, the absorbance at the wavelength of 492 nm was measured by using a multiwell plate reader (MODEL 2550EIA READER, manufactured by BIO-RAD) with the use of air as the blank.

DETERMINATION OF ANTIBODY TITER:

In the measurement of the antibody titers of the antisera, the absorbance of a normal non-immune serum was also measured as a negative control. The maximum dilution of the antiserum-containing well showing an absorbance of at least 0.35 was referred to as the antibody titer of the corresponding antiserum. In the screening, hybridomas, the culture supernatant of which showed an absorbance comparable to or exceeding that of the positive control with respect to WA0322-1 but no reactivity with WA0322-2, were referred to as antibody-producing hybridomas.

Example 4
(Determination of subclass of monoclonal antibody thus produced)

The subclasses of the monoclonal antibodies produced by the hybridomas constructed above were determined in accordance with the ELISA method of Example 3 with the use of Mouse Mono AB ID kit (HRP) (manufactured by ZYMED).

The culture supernatant of hybridomas was reacted with the ELISA plate having the WA0322-1 solid phase. Further, antibodies (rabbit) specific respectively to the mouse immunoglobulin classes and subclasses (IgG1, IgG2a, IgG2b, IgG3, IgA, IgM, Igkappa and Iglambda) were reacted therewith. After reacting with the enzyme-labeled antirabbit antibody, detection was carried out through the enzyme reaction. Simultaneously, the same measurement was performed but using normal non-immune rabbit serum as a negative control instead of the antibody specific to each subclass. A sample showing twice or more absorbance than that of the negative control was referred to as positive.

Table 2 summarizes the results thus obtained. Among the obtained antibodies, 1E7, 1E9, 1G5, 1G12 and 2H7 corresponded to IgG1, 2H9 corresponded to IgG2a and 3E7 corresponded to IgM.

TABLE 2

Class and Subclass of each monoclonal antibody

| Type of antibody | 1E7 | 1E9 | 1G5 | 1G12 | 2H7 | 2H9 | 3E7 |
|---|---|---|---|---|---|---|---|
| IgG1 | 11.4 | 5.49 | 4.10 | 6.14 | 4.67 | 1.13 | 1.01 |
| IgG2a | 0.93 | 1.51 | 1.31 | 1.53 | 1.48 | 11.4 | 1.02 |
| IgG2b | 0.73 | 0.77 | 0.79 | 1.00 | 1.13 | 1.46 | 1.17 |
| IgG3 | 0.90 | 1.05 | 0.97 | 1.25 | 1.30 | 1.17 | 1.23 |
| IgA | 0.75 | 1.27 | 1.11 | 1.53 | 1.57 | 1.34 | 1.27 |
| IgM | 1.10 | 1.23 | 1.00 | 1.44 | 1.26 | 0.98 | 11.0 |
| Ig kappa | 11.4 | 5.70 | 3.54 | 5.20 | 4.88 | 11.4 | 9.93 |
| Ig lambda | 1.23 | 1.40 | 1.08 | 1.38 | 1.24 | 1.25 | 1.87 |
| NRS* ($A_{492}$) | 0.176 | 0.182 | 0.217 | 0.154 | 0.157 | 0.175 | 0.181 |
| Classification | IgG1 | IgG1 | IgG1 | IgG1 | IgG1 | IgG2a | IgM |

Each value given in the above table but those of NRS has the following meaning:
Value = absorbance of well with antibody of each class or subclass/ absorbance of well with NRS.
*non-immune rabbit serum (negative control).

Example 5
(Reactivities of hybridoma culture supernatant with WA0322-1 and WA0322-2)

By using the ELISA method as described in Example 3, the reactivity of each culture supernatant was examined. In this examination, use was made of plates having WA0322-1 and WA-0322-2 solid phases. As a negative control, the culture supernatant of P3U1 was employed.

Figure 1B:
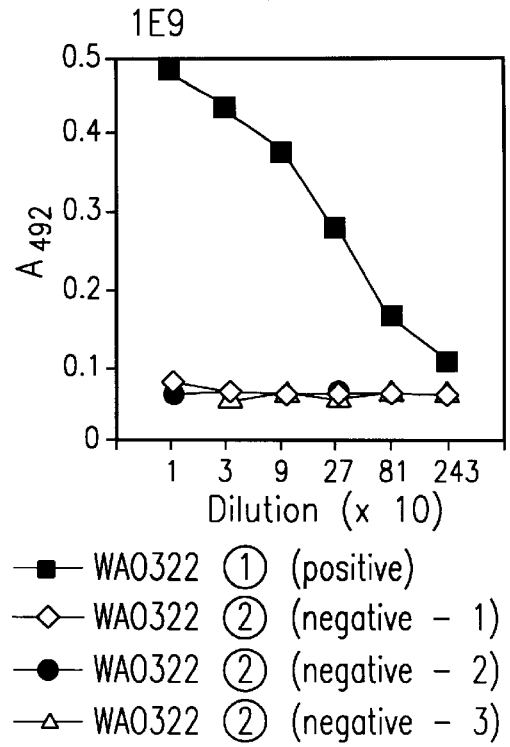
Figure 1C:
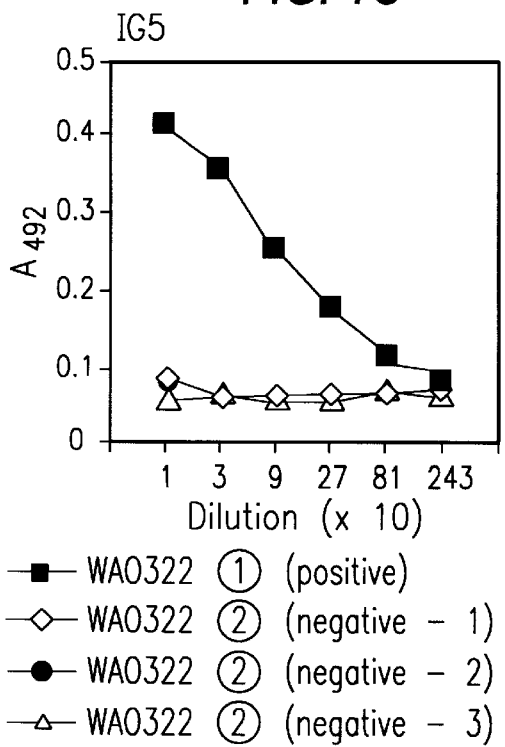
Figure 1D:
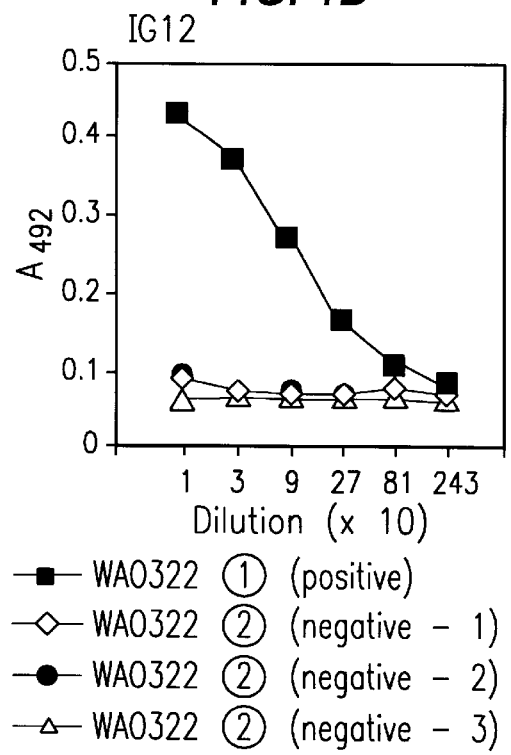
Figure 2A:
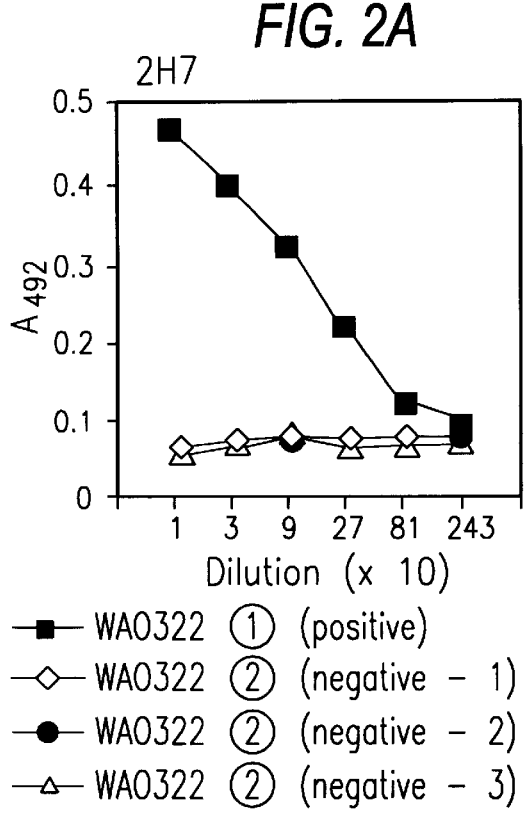
FIGS. 2A–2D are graphs showing the reactivity to the antigen of each of the monoclonal antibodies (2H7, 2H9 and 3E7) and the P3U1 culture supernatant employed as a control.
Figure 2B:
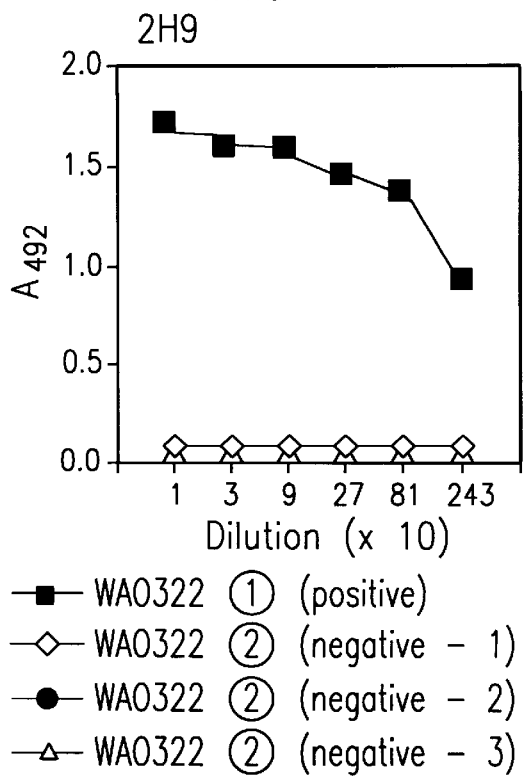
Figure 2C:
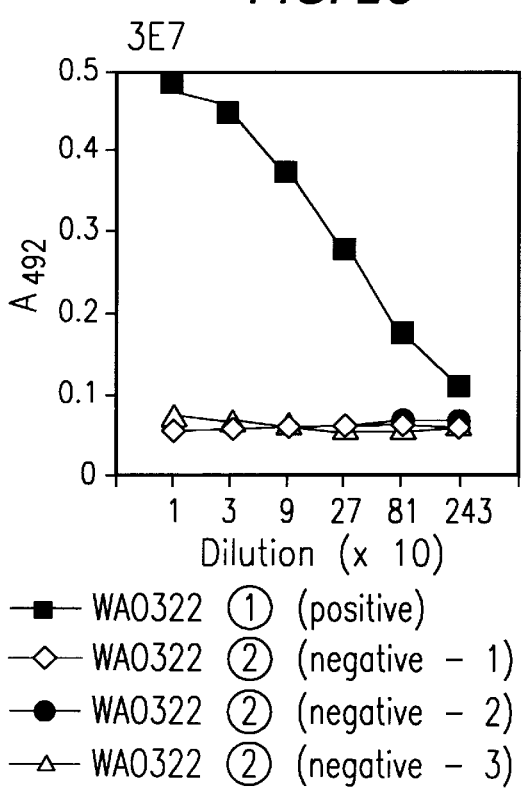
Figure 2D:
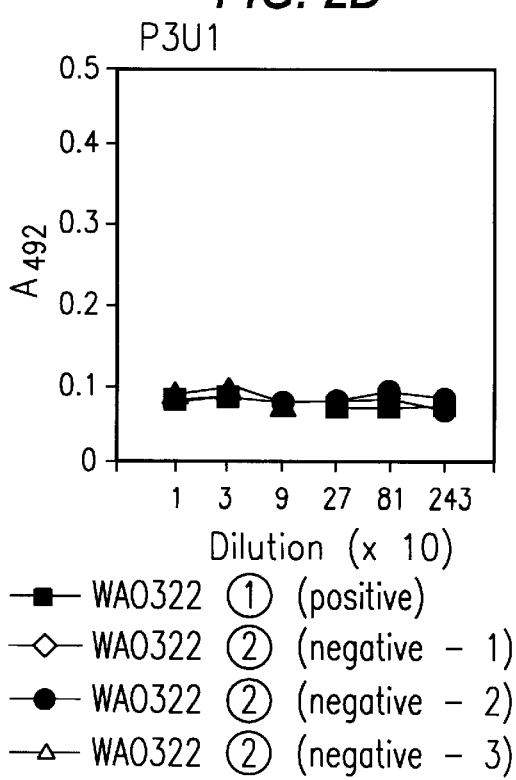

FIGS. 1 and 2 show the results thus obtained. The obtained 7 antibodies all reacted with not WA0322-2 but WA0322-1. These results indicate that all of the obtained antibodies react specifically with WA0322-1.

INDUSTRIAL APPLICABILITY

As is understood from the above description, the monoclonal antibody of the present invention has a high reactivity with the adeno-associated virus CAP protein.

Accordingly, by utilizing the advantage of the monoclonal antibody provided by the present invention, i.e., the characteristic of being capable of specifically recognizing the adeno-associated virus and a recombinant adeno-associated virus vector, this novel monoclonal antibody can be applied as follows. That is to say, this monoclonal antibody is applicable to the detection of the adeno-associated virus and the purification of recombinant adeno-associated virus vectors for gene therapy.

Moreover, there has been successfully established a hybridoma cell line capable of specifically producing the monoclonal antibody against adeno-associated virus CAP protein, which makes it possible to easily obtain the monoclonal antibody on a mass scale.

We claim:

1. A monoclonal antibody specifically recognizing the adeno-associated virus CAP protein, wherein said monoclonal antibody is produced from a hybridoma cell line selected from the group consisting of: HAAV-1G12; HAAV-1E9; HAAV-2H7; HAAV-2H9; HAAV-1G5; HAAV-3E7; and HAAV-1E7.

2. A hybridoma cell line capable of producing a monoclonal antibody specifically recognizing the adeno-associated virus CAP protein, wherein said hybridoma cell line is selected from the group consisting of: HAAV-1G12; HAAV-1E9; HAAV-2H7; HAAV-2H9; HAAV-1G5; HAAV-3E7; and HAAV-1E7.

3. A method of detecting adeno-associated virus comprising: contacting a biological sample with monoclonal antibody specifically recognizing the adeno-associated virus CAP protein; and detecting the presence or the absence of binding of the monoclonal antibody as an indication of the presence or absence of an adeno-associated virus in the biological sample, wherein said monoclonal antibody is produced from a hybridoma cell line selected from the group consisting of: HAAV-1G12; HAAV-1E9; HAAV-2H7; HAAV-2H9; HAAV-1G5; HAAV-3E7; and HAAV-1E7.

4. A method of purifying an adeno-associated virus recombinant vector for gene therapy comprising: contacting a sample comprising an adeno-associated virus recombinant vector with a monoclonal antibody specifically recognizing the adeno-associated virus CAP protein, wherein said monoclonal antibody is produced from a hybridoma cell line selected from the group consisting of HAAV-1G12; HAAV-1E9; HAAV-2H7; HAAV-2H9; HAAV-1G5; HAAV-3E7; and HAAV-1E7, and wherein the sample and antibody are subjected to suitable conditions for the binding of said antibody to said CAP protein; and eluting said adeno-associated virus recombinant vector with a suitable eluent.

* * * * *